United States Patent [19]

Nagata et al.

[11] Patent Number: 5,246,664
[45] Date of Patent: Sep. 21, 1993

[54] WATER-DISINTEGRABLE MATERIAL AND DEVICE FOR ASSAYING A BODY FLUID

[75] Inventors: Ryohei Nagata; Tskeshi Saito; Tetsuya Fujiwara; Motohiro Oka; Masanao Watanabe, all of Tokyo, Japan

[73] Assignee: Dai Nippon Insatsu Kabushiki Kaisha, Japan

[21] Appl. No.: 651,252

[22] PCT Filed: Jul. 31, 1990

[86] PCT No.: PCT/JP90/00976

§ 371 Date: May 20, 1991

§ 102(e) Date: May 20, 1991

[87] PCT Pub. No.: WO91/02249

PCT Pub. Date: Feb. 21, 1991

[30] Foreign Application Priority Data

Aug. 10, 1989 [JP] Japan .................. 1-205656
Aug. 29, 1989 [JP] Japan .................. 1-222624
Aug. 29, 1989 [JP] Japan .................. 1-222625
Aug. 29, 1989 [JP] Japan .................. 1-222626

[51] Int. Cl.⁵ .................. G01N 21/78; G01N 33/50
[52] U.S. Cl. .................. 422/56; 422/55; 422/57; 435/805
[58] Field of Search .................. 422/56, 57, 58, 55, 422/60; 436/170, 172; 435/7.1, 7.93, 805

[56] References Cited

U.S. PATENT DOCUMENTS

| | | | |
|---|---|---|---|
| 4,255,384 | 3/1981 | Kitajima et al. | 422/57 |
| 4,478,944 | 10/1984 | Gross et al. | 422/56 |
| 4,540,670 | 9/1985 | Arai et al. | 436/170 |
| 4,587,102 | 5/1986 | Nagatomo et al. | 422/56 |
| 4,594,224 | 6/1986 | Okaniwa et al. | 422/56 |
| 4,870,005 | 9/1989 | Akiyoshi et al. | 435/7.93 |
| 5,071,623 | 12/1991 | Akutsu | 422/56 |

OTHER PUBLICATIONS

Chemical Abstracts, vol. 113, No. 15, Oct. 8, 1990, p. 333, col. 2, Abstract No. 128974q, Columbus Ohio & JP-A-02 78 956 (Matsushita Electric Works, Ltd) Mar. 19, 1990.

Patent Abstracts of Japan, vol. 10, No. 106 (P-449) [2163], Apr. 22, 1986 & JP-A-60 238 763 (Dainippon Insatsu K.K.) Nov. 27, 1985.

Patent Abstracts of Japan vol. 11, No. 201 (P-590) [2648], Jun. 30, 1987 & JP-A-62 24 145 (Terumo Corp.) Feb. 2, 1987.

*Primary Examiner*—James C. Housel
*Assistant Examiner*—Long V. Le
*Attorney, Agent, or Firm*—Parkhurst, Wendel & Rossi

[57] ABSTRACT

A water-disintegrable support paper material largely formed of fibrous carboxymethylcellulose or carboxyethylcellulose having a degree of etherification of 0.1 to 1.0 and a degree of base saturation of 20% or more. A solution or dispersion of that paper has a pH of 5.0 to 8.0. There is also disclosed a composition for forming a water-disintegrable coat for coating on the support, the composition being a mixture of (a) at least one water-insoluble resin capable of forming a film having a saturation hygroscopicity less than 15% at a 90% relative humidity, (b) at least one water-soluble resin capable of forming film having a saturation hygroscopicity of 15% or more at a 90% relative humidity, and (c) a solvent in which both the resins (a) and (b) can dissolve. Lastly, there is disclosed a device for assaying a body fluid obtained by providing a body fluid assay reagent layer on at least a part of the coat on the support material, giving the device improved maneuverability and toughness during inspection and improved disintegrability after use.

8 Claims, No Drawings

WATER-DISINTEGRABLE MATERIAL AND DEVICE FOR ASSAYING A BODY FLUID

TECHNICAL FIELD

The present invention concerns a water-disintegrable material and its use. More specifically, this invention relates to a material which can be disintegrated (solubilized or swelled) by water to such an extent that it can be allowed to flow in water, although it retains a complete coat form for a certain short time in water. For instance, this material may be used as formats for confidential papers, frames for raising rice seedlings, seeding sheets, seedling sheets, water-soluble water absorption paper, materials for body fluid assay devices or kits, and so on. Before or during use, that material plays a recording medium, delivery, protection or other role while keeping its original form and, after that, it is eventually allowed to be dissolved and dispersed in water for disposal.

BACKGROUND ART

Water-soluble and -swelling resin coats designed to flow in water are made of such resins as polyvinyl alcohol, polyvinyl pyrrolidone and viscose with the aid of coating agents.

The aforesaid resin coats made of water-soluble resins by and large are satisfactory in terms of being capable of being allowed to flow in water.

However, in some applications where resin coats are required to retain their film forms stably in water for an initial certain short time without being swollen on their surfaces, there are diverse demands toward their minimum non-swelling time in water, depending upon what they are used for. Moreover, there are different requirements for how much soluble or swollen resin coats should be in water so as to be eventually allowed to flow in water, for instance, between industrial waste water disposal and life-related waste water disposal. A great deal of difficulty is thus involved in forming resin coats meeting such different requirements of a single resin.

For instance, water-soluble and-dispersible fibrous materials used as the supports of body fluid assay kits or devices are required to retain their resin coats stably in water for a certain, if not long, period of time. Yet it is very difficult to form a resin coat meeting such a requirement in a simple manner.

Until now, the supports for the aforesaid body fluid assay kits have been made of plastic sheets such as polystyrene sheets, because they should have a suitable degree of rigidity. However, such plastic sheet supports cannot be disposed of in toilet facilities after use, since they are neither soluble nor dispersible in water. Thus, it is a nuisance for the users to throw away them hygienically after use.

For that reason, body fluid assay devices comprising a test piece sheet of such water-soluble resins as polyvinyl alcohol and polyvinyl pyrrolidone (Japanese Patent Kokai Publication No. 62-24145) or a support obtained by making use of paper obtained by processing a fibrous component comprising pulp or regenerated pulp and a binder component comprising such a water-soluble resin as carboxymethylcellulose (Japanese Patent Laid-Open Publication No. 60-238763) by the paper-making technique have been proposed as toilet-disposable, water-dispersible body fluid assay devices.

In the first-mentioned body fluid assay device in which the support is made of a water-soluble resin, it is required that a plurality of films of the aforesaid water-soluble resin be laminated together in order for that support to retain the sufficient rigidity required for that body fluid assay device. This body fluid assay device is not only troublesome to assemble, but a time as long as 30 minutes or more is also needed for it to dissolve and disperse in water, when it has a thickness sufficient to achieve the aforesaid rigidity.

On the other hand, the second-mentioned body fluid assay device, whose support is made of paper obtained by the paper-making process using a fibrous component comprising pulp or regenerated pulp and a binder component of such a water-soluble resin as carboxymethylcellulose, is easy to handle because, once used, it can be disposed of in toilet facilities. A problem with this device, however, is that when the support is to be coated as by printing with an assay reagent layer, optionally with the reference color layer for determination, printing ink is likely to penetrate through the support. This makes it difficult to coat on the support the desired assay reagent layer optionally with the reference color layer for determination.

Some additional versions of body fluid assay devices have been proposed in Japanese Patent Laid-Open Publication Nos. 60-238763 and 1-121752, which include a support obtained by coating or laminating a water-soluble resin on either or both sides of paper prepared by the paper-making process using a fibrous component comprising pulp or regenerated pulp and a binder component of such a water-soluble resin as carboxymethylcellulose. These are said to retain shape during use and be disposable in toilet facilities.

However, the inventors' finding teaches that when a body fluid assay device making use of this support is immersed in a body fluid sample over too long a period of time, it cannot retain shape and tends to drop in terms of post-immersion rigidity. Thus, that body fluid assay device is less than satisfactory in terms of shape retention, since it sags at its end within the time of about 60 seconds required for coloration. Especially when a urine sample is injected directly onto the its reagent carrying region, its support is apt to suffer damage and so is less than satisfactory.

DISCLOSURE OF THE INVENTION

The present invention provides a body fluid assay device, wherein (a) while the support region possesses rigidity sufficient to serve as a support therefor, (b) it is so well dispersible or soluble in water that the assay unit can be flushed down the toilet (c) a given assay reagent layer together with a control reference color layer is orderly applied on the support's surface by coating without causing penetration of printing ink therethrough, and (d) an increased adhesion strength is obtained between the support and the coat layer providing the assay reagent layer, and (e) the device possesses such toughness as to enable a fluid body sample to be injected from a syringe onto the reagent layer, i.e. such toughness as to a sample, e.g. a urine sample to be inspected by injecting it onto the reagent layer, not via a separate vessel such as a cup, and a material therefor.

The water-disintegrable support material according to this invention comprises paper composed mainly of fibrous carboxymethylcellulose or carboxyethylcellulose having an etherification degree of 0.1 to 1.0 and prepared by the paper-making process, and characterized in that the fibrous carboxymethylcellulose or carboxyethylcellulose forming a major part of said support material has a degree of base saturation of 20% or more and a solution or dispersion of said paper is in the pH range of 5.0 to 8.0.

A composition for forming a water-disintegrable film, which is to be coated on the aforesaid support according to this invention, is characterized by comprising a mixture of (a) at least one water-insoluble resin capable of forming a film having a saturation hygroscopicity less than 15% at a 90% relative humidity with (b) at least one water-soluble resin capable of forming a film having a saturation hygroscopicity of 15% or higher at a 90% relative humidity, and (c) a solvent in which said resins (a) and (b) can dissolve.

The water-disintegrable substrate according to this invention is obtained by forming a coat layer comprising the aforesaid composition on the aforesaid support. It is understood that the coating layer or layers may be coated or otherwise laminated on either or both sides of the support.

A device for assaying a body fluid may be obtained by forming a body fluid assay reagent layer on at least a part of the aforesaid coating layer(s) of the substrate.

BEST MODE FOR CARRYING OUT THE INVENTION

In what follows, the present invention will be explained more illustratively with reference to the components used for the preparation of the body fluid assay device.

It is to be understood that while the body fluid assay unit according to this invention may take various forms such as sheets and strips, the present invention will now be described with reference to the strip type of body fluid assay device.

For the purpose of detecting, diagnosing and treating various diseases, examination is often made of whether or not such body fluids as urine, blood and lymph contain such ingredients as glucose and protein, their content and pH, and so on. Used to this end are body fluid assay strips in which the supports carry various assay reagent layers, optionally with reference color layers for determination.

For the water-soluble and-dispersible, fibrous supports of body fluid assay strips, use may be made of, e.g.:

1) paper made by the paper-making process in which reclaimed pulp or pulp is formed into paper using such a water-soluble resin as carboxymethylcellulose as a binder;

2) paper obtained by the paper-making process from papermaking materials in which the major fibrous component is fibrous carboxymethylcellulose or carboxyethylcellulose having a degree of etherification in the range of 0.1 to 1.0; and 3) paper made by the paper-making process, in which the major fibrous component or the aforesaid fibrous carboxymethylcellulose or carboxyethylcellulose is regulated to 20% or more in terms of the degree of base saturation, and which provides a solution or dispersion with its pH lying in the range of 5.0 to 8.0.

Of the above-mentioned paper materials, the greatest preference is given to the paper (3) composed mainly of fibers, in which the fibrous carboxymethylcellulose or carboxyethylcellulose is adjusted to a degree of base saturation of 20% or more and which provides a solution or dispersion with its pH lying in the range of 5.0 to 8.0. This is because the best results of examination are obtained since the pH of the sample to be inspected with the body fluid assay strip is not affected by the support itself.

For instance, the detection of glucose in body fluids makes use of the reaction of the glucose with atmospheric oxygen under the action of glucose oxidase or other oxidase, by which it is eventually oxidized into gluconic acid and hydrogen peroxide. The thus formed hydrogen peroxide produces nascent oxygen under the action of peroxidase. Then, this oxygen is allowed to react with an indicator to be oxidized such as guaiac fat or o-tolidine. Whether or not the glucose is found or its quantity is determined by the degree of color of the indicator.

For the detection of glucose based on this reaction, the indicator carried on a support is usually adjusted to such an acidic pH as to effect a preferable color change in a reagent layer for detecting glucose.

The detection of protein in body fluids relies upon the principles, according to which as a protein detecting indicator whose pH is maintained on an acidic side, such as Tetrabromophenol Blue, Tetrabromothymol Blue or tetraphthalein ether ester forms a complex with the protein contained in body fluids, it turns from acidic yellow to basic blue. The quantity of protein in body fluids is determined by how discolored that indicator is.

Thus, the protein detecting reagent layer carried on a support must be maintained on an acidic pH side at an initial stage of the reaction.

The detection of urobilinogen in body fluids is based on the principles, according to which as that urobilinogen reacts a complex with p-di(alkyl)aminobenzaldehyde to form a complex, it shows an yellowish pink to reddish purple color depending upon what concentration that urobilinogen is in. The urobilinogen detecting reagent layer carried on a support must again be maintained on an acidic pH side in an early stage of the reaction.

When detection is carried out with a body fluid assay strip comprising a support and a reagent layer carried thereon, it is not that only the reagent layer comes into contact with the body fluids to be tested. In other words, that reagent layer with the support is brought into contact with the body fluids. Hence, if the pH of the body fluids is likely to change by contact with the support, then it would mislead the obtained results of inspection.

According to the body fluid assay strip of this invention, the paper preferably used as its support is composed mainly of fibrous carboxymethylcellulose and/or fibrous carboxyethylcellulose which have a degree of etherification lying in the range of 0.1 to 1.0. Alternatively, the fibrous carboxymethylcellulose or carboxyethylcellulose having a degree of etherification lying in the range of 0.1 to 1.0 may be mixed with other paper-making fibrous components such as paper-making kraft pulp or sulfite pulp, rayon pulp, polyamide fibers and polyester fibers.

In the case of the latter paper obtained from mixed other fibers, however, it is preferred that the other fibrous components be used in an amount of 50 parts by weight or less per 100 parts by weight of the above-mentioned carboxymethylcellulose plus carboxyethylcellulose components. This is because in an amount exceeding 50 parts by weight, the resulting paper tends to degrade in its dispersibility in water.

It is also required that the degrees of etherification of the carboxymethylcellulose and carboxyethylcellulose forming a major part of the paper be 0.1 or more, because at below 0.1 the resulting paper becomes less than satisfactory in terms of its water dispersibility and solubility. In this connection, it is noted that when the carboxymethylcellulose and carboxylethylcellulose have a degree of etherification of 0.65 or more, the fibers swell so vigorously that papermaking is troublesome. However, if no weight is attached to the paper-making speed, it is then possible to make use of material having a degree of etherification of at most 1.0.

However, preference is usually given to using fibrous carboxymethylcellulose or carboxylethylcellulose having a degree of etherification of 0.40 to 0.60 in view of paper-making considerations as well as the water dispersibility and solubility and strength of the resulting paper.

In the paper forming part of the support for the body fluid assay strip according to this invention, the aforesaid carboxymethylcellulose or carboxyethylcellulose is preferably adjusted to a degree of base saturation of 20% or more. This is because at less than 20% it is impossible to obtain paper having such water dispersibility and solubility as to be flushed down the toilet.

It is noted that the regulation of the degree of base saturation of the fibrous carboxymethylcellulose or carboxylethylcellulose forming a major fibrous part of the above-mentioned paper, the pH regulation of the surface of the above-mentioned paper to be provided with a reagent layer and the pH regulation of a solution or dispersion of the above-mentioned paper are easily achievable in the steps of processing into paper the paper-making material composed mainly of the fibrous carboxymethylcellulose or carboxyethylcellulose having a degree of etherification of 0.1 to 1.0. In other words, these are attainable by a first paper-making step in which an aqueous solution of an alkali metal compound such as carbonate of soda or caustic soda is added to wet paper on felt in a slightly excessive amount (more than the neutralization equivalent of the carboxymethylcellulose or carboxyethylcellulose in the wet paper) to obtain dry paper of about pH 10-11 in which fibrous cellulose glycolate is converted into salts of such metals as Na through ion exchange, and a second step in which the obtained dry paper is treated by a dilute acid.

More specifically, if the aqueous solution of the alkali metal compound is added to the wet paper on felt during the paper-making course of processing a papermaking feed composed mainly of fibrous carboxymethylcellulose or carboxyethylcellulose, then the above-mentioned dry paper can be obtained by continuous operation without inflicting on the wet paper such damages as incidental cutting, since the above-mentioned felt serves as a reinforcing belt for the wet paper.

It is noted that if an aqueous solution containing an organic solvent such as methanol or acetone is used as the above-mentioned aqueous solution of the alkali metal compound, it is then possible to more effectively prevent the wet paper from suffering damage in the course of the above-mentioned alkali treatment.

In the second or acid treatment step wherein the paper material of about pH 10-11, in which the major fibrous component is formed of the metal, e.g. Na, salt of fibrous cellulose glycolate, is impregnated with a dilute acid to effect local formation of fibrous cellulose glycolate, a dilute acid solution, e.g. a dilute hydrochloric acid solution may be applied uniformly to the paper, while regulating its pH. However, this often causes the reverse reaction of —COOH —COONa to take place locally and noticeably, in which case difficulty will be encountered in forming uniform fibrous cellulose glycolate having a degree of base saturation of 20% or more.

For that reason, the above-mentioned acid treatment is preferably carried out with a solution obtained by dissolving an organic acid in a mixed solvent of water with an organic solvent, said organic acid having an acid-in-water index or pKa—the cologarithm of its dissociation in water—increased to 3 or more.

More specifically, when the acid treatment is carried out with the solution in which an organic acid having an acid-in-water index increased to 3 or more is dissolved in a mixed solvent of water with an organic solvent, it is possible to effectively limit the extent of a lowering of the degree of base saturation of the metal, e.g. Na, salt of fibrous cellulose glycolate. To this end, use is preferably made of an about 0.3 to 10 wt. % solution of an acid having an acid-in-water index increased to 3 or more, such as acetic, succinic, lactic, glycolic, malic or tartaric acid, in the mixed solvent of water with an organic solvent.

It is noted that the preferred organic solvent in the above-mentioned mixed solvent is an alcohol such as methyl alcohol, ethyl alcohol, propyl alcohol and butyl alcohol; acetone; methyl ethyl ketone; methyl propyl ketone; and so on. For the reason that the presence of the abovementioned organic solvent in the mixed solvent plays a role in limiting the extent of a decrease in the base saturation of the above-mentioned fibrous carboxymethylcellulose or carboxyethylcellulose, the mixed solvent preferably contains more than 30 wt. % of the organic solvent.

It is noted that while the degree of base saturation of the fibrous carboxymethylcellulose or carboxyethylcellulose obtained at the above-mentioned acid treatment step is determined by the degree of etherification of carboxymethylcellulose or carboxyethylcellulose, the type of the acid available, the acid-in-water index of the acid available, the composition of the mixed solvent, the acid concentration of the processing solution and the coating rate of the processing solution. However, this is primarily determined by the acid concentration of the processing solution, if the rest is all identical. By performing the acid treatment under the conditions determined by preliminary experimentation, it is thus possible and advantageous to obtain paper in which the fibrous carboxymethylcellulose or carboxyethylcellulose forming its major fibrous part has a degree of base saturation maintained at 20% or more and which, upon disintegrated by water, provides a solution or dispersion whose pH lies in the range of 5.0 to 8.0.

A water-soluble and -dispersible resin coat or coats formed on either or both sides of the above-mentioned water-dispersible and -soluble fibrous substrate is or are provided with an assay reagent layer formed of, e.g. a mixed resin of polyvinyl pyrrolidone with polyvinyl butyral, said assay reagent layer being firmly and integrally bonded thereto.

In what follows, the water-disintegrable composition will be explained.

According to one aspect of this invention, there is provided a coat-forming composition comprising a mixed resin of at least one water-insoluble resin capable of forming a film having a saturation hygroscopicity less than 15% at a 90% relative humidity with at least one water-soluble resin capable of forming a film having a saturation hygroscopicity of 15% or more at a 90 relative humidity, and a solvent in which both the resins can dissolve.

According to another aspect of this invention, there is provided a coat forming composition as mentioned above, wherein the mixed resin in a solvent solution comprises polyvinyl pyrrolidone and polyvinyl butyral.

According to a further aspect of this invention, there is provided a coat-forming composition as mentioned above, the mixed resin in a solvent solution comprises 95 to 50 parts by weight of polyvinyl pyrrolidone with 5 to 50 parts by weight of polyvinyl butyral According to a still further aspect of this invention, there is provided a coat-forming composition as mentioned in any one of the 1st to 3rd aspects, wherein the solvent is an alcohol such as amyl alcohol.

In the coat-forming compositions according to this invention, the resin capable of forming a film having a saturation hygroscopicity less than 15% at a 90% relative humidity is a hydrophobic resin. For example, use is preferably made of the following resins.

| Type of Film | Saturation Hygroscopicity |
| --- | --- |
| Polyisobutyl ether | 1.2% |
| Polymethyl methacrylate | 1.4% |
| Polyvinyl acetate | 3.1% |
| Polyvinyl butyral | 3.5% |
| Cellulose acetate with a degree of substitution or DS of 2.3 | 10.5% |

The resin capable of forming a film having a saturation hygroscopicity of 15% or more at a 90% relative humidity is a hydrophilic resin. For instance, use is preferably made of the following resins.

| Type of Film | Saturation Hygroscopicity |
| --- | --- |
| Sodium polyacrylate | 151.7% |
| Polyvinyl pyrrolidone | 67.9% |
| Polyacrylic acid | 47.5% |
| Polyvinylmethoxy acetal with an acetal content of 48% | 42.3% |
| Polyvinylamine (75% RH) | 39.5% |
| Polyvinyl alcohol | 26.4% |
| Viscose | 22.1% |
| Cellulose acetate with a DS of 0.8 | 22.0% |
| Polyethylene oxide | 18.0% |
| Polyvinylmethoxy acetal with an acetal content of 86% | 16.3% |

In the present invention, not only such alcohols as mentioned above but also hydrophilic group-containing organic solvents such as dioxane and anisole may be used as the solvent in which the above-mentioned two resins can dissolve.

The coat-forming composition—one embodiment of this invention—applied to the above-mentioned water-dispersible and -soluble fibrous substrate is provided to retain the surface of the support provided with an assay reagent layer in the form of a complete film in water for a certain short period of time. For instance, when the assay reagent layer is formed of a coat layer, it serves to prevent the coating agent for forming the coat layer from penetrating through the support.

When the coat-forming composition formed of the mixed resin of polyvinyl pyrrolidone with polyvinyl butyral—one embodiment of the coat-forming composition according to this invention—is used for a body fluid assay strip, that mixed resin should not contain 95% by weight or less of polyvinyl pyrrolidone. This is because at more than 95% the support's surface is so poor in toughness that it is drastically broken when a body fluid sample is injected directly onto the body fluid assay strip.

When the resin coat-forming mixed resin of polyvinyl pyrrolidone with polyvinyl butyral contains less than 50 by weight of polyvinyl pyrrolidone, the support cannot be flushed down the toilet due to its decreased water-solubility and -dispersibility.

EXAMPLE A

A mixed feed of 80 parts by weight of fibrous carboxymethylcellulose having a degree of etherification of 0.54 and 20 parts by weight of bleached kraft pulp was processed to a degree of beating of 20° SR into a starting material for paper making. This starting material was formed into sizeless paper at a rate of 20 m/min by means of a cylinder paper machine, while an 8% by weight aqueous solution of carbonate of soda was coated on the wet paper being formed, thereby obtaining alkaline paper (a) having a weight of 120 g/m$^2$.

Subsequently, a 1.25% by weight dilute acid solution of acetic acid and citric acid (at a weight ratio of 2:3) dissolved in a mixture of equal amounts of methanol and water was roll-coated on the paper (a) to a coverage of 1.9 g/m$^2$, calculated as acid matter, followed by drying. In this way, neutral paper (b) was obtained, which formed part of the support of a body fluid assay strip according to one embodiment of this invention.

The thus obtained paper (b) shows pH 5.8 on its acid treated surface, and provides an aqueous dispersion of pH 7.2. The alkaline paper (a) has a volume of base substitution of 2.79 meq/g (as calculated), and the neutral paper (b) shows a degree of base saturation of 65.1%.

(a) COMPARATIVE EXAMPLE A

A bleached kraft pulp feed having a degree of beating of 20° SR was processed into comparative paper (c) having a weight of 120 g/m$^2$ at a rate of 20 m/min by means of a cylinder paper machine.

Experiment 1

About 500 cc of water placed in a beaker were agitated by means of a stirrer until stable, 3 to 4-cm high vortices were obtained. Then, a strip of 8 × 80 mm of each of the paper (b) obtained in Example A, the paper (c) obtained in Comparative Example A and the paper (a) obtained in the course of Example A was put in the water to determine its water dispersibility.

The results are given below.
Paper (a) ... Outstandingly good
Paper (b) ... Good
Paper (c) ... Bad

Experiment 2

The paper (a) obtained in Example A, the paper (c) obtained in Comparative Example A and the paper (a) obtained in the course of Example A were each used as the support of a pH indicator. To this end, the following ink composition was screen-printed on the support in the form of a reagent layer.

It is noted that for printing the aforesaid reagent layer, an 80-mesh screen printing plate was used, with the total thickness of the resist and screen gauze being 190 μm. Ink Composition for pH Detection (in parts by weight p.b.w. for short)

| | |
|---|---|
| Methyl Red | 0.070 p.b.w. |
| Bromothymol Blue | 1.0 p.b.w. |
| Dodecyltrimethylammonium chloride | 1.0 p.b.w. |
| Polyvinyl pyrrolidone | 8.3 p.b.w. |
| Polyvinyl butyral | 4.1 p.b.w. |
| Fine cellulose powders | 174.0 p.b.w. |
| Butyl Cellosolve | 226.9 p.b.w. |
| Butyl Cellosolve acetate | 22.0 p.b.w. |
| Sodium hydroxide | 0.098 p.b.w |
| Water | 2.0 p.b.w. |

Furthermore, dilute hydrochloric acid and caustic soda solutions were added to normal urine to prepare urine samples regulated to pH 5, 6, 7, 8 and 9. The aforesaid three pH indicator papers were immersed in these samples. The indicator paper using the paper (b) as the support was colored in the same pH color as that on a separately provided control table, but the indicators using the papers (a) and (c) as the supports were in no agreement with the corresponding colors on the control table.

The present supports for body fluid assay strips each contain as the main fibrous component fibrous carboxymethylcellulose or carboxyethylcellulose having a degree of etherification of 0.1 to 1.0, with the degree of base saturation being adjusted to 20% or more. Thus, they are well dissolved or dispersed in water and have some thickness enough to meet the suitable rigidity required for supports forming part of body fluid assay strips to have, yet they can be disposed of in toilet facilities after use.

Accordingly, the body fluid assay strips comprising the present supports have some advantages of being easy for the users to dispose of, being sanitary, and so on.

As mentioned above, the paper forming part of the support according to this invention provides a solution or dispersion with its pH ranging from 5.0 to 8.0. Thus, when measuring the pH of the body fluids to be examined or assaying body fluids with the use of reagent layers preregulated to acidity, like those for detecting glucose, protein, urobilinogen, etc., the pH of the region to be examined is unlikely to be affected by the support itself.

With the body fluid assay strip comprising the present support, therefore, it is possible to obtain precise results of examination without causing pH changes, which may otherwise take place due to body fluid assay strips, to be reflected in the reaction of the reagent layer.

EXAMPLE B

In the description that follows, the illustrative construction of the composition for forming a coat according to this invention and how to use it will be explained with reference to an embodiment in which said composition is applied to the support of a body fluid assay strip.

Water-Dispersible and -Soluble, Fibrous Material

A mixed feed of 80 parts by weight of fibrous carboxymethylcellulose having a degree of etherification of 0.54 and 20 parts by weight of bleached kraft pulp was processed to a degree of beating of 20° SR into a starting material for paper making. This starting material was formed into sizeless paper at a rate of 20 m/min by means of a cylinder paper machine, while an 8% by weight aqueous solution of carbonate of soda was coated on the wet paper being formed, thereby obtaining alkaline paper (A) having a weight of 120 g/m².

Subsequently, a 1.25% by weight dilute acid solution of acetic acid and citric acid (at a weight ratio of 2:3) dissolved in a mixture of equal amounts of methanol and water was roll-coated on the paper (A) to a coverage of 1.9 g/m², calculated as acid matter, followed by drying. In this way, neutral paper (B) was obtained.

The thus obtained paper (B) shows pH 5.8 on its acid treated surface, and provides an aqueous dispersion of pH 7.2. The alkaline paper (A) has a volume of base substitution calculated to be 2.79 meq/g, and the neutral paper (B) shows a degree of base saturation of 65.1 %.

Formation of Resin Coat on the Surface of Fibrous Material

Using a mixed resin of 90 parts by weight of polyvinyl pyrrolidone—a linear chain polymer of 1-vinyl-2-pyrrolidone having a mean polymerization degree of about 11,000; Colidone 90 made by BASF AG. and 10 parts by weight of polyvinyl butyral—having a polymerization degree of about 1,700 and a butylation degree of about 65 mol %; Eslec B made by Sekisui Chemical Co., Ltd.), the aforesaid neutral paper (B) was provided on both its sides with resin coats to a coverage of 5.0 g/m² on dry matter basis.

Reference will now be made to the coating agent and manner used for forming the aforesaid coats.

Coating Agent

To obtain this, a given amount of a well-stirred mixture of 15% by weight polyvinyl pyrrolidone with amyl alcohol and a given amount of a well-stirred mixture of 15% by weight of polyvinyl butyral with amyl alcohol, both mixtures obtained with the use of a homomixer, were fully mixed together by means of a spatula.

Coating Manner

Coating was carried out with the use of a Miya bar No. 6.

The obtained support for a body fluid assay strip has a water dispersibility enough to be flushed down the toilet, and possesses such a surface toughness so as to enable a body fluid sample to be injected from a syringe onto the reagent layer formed thereon, i.e. such a surface toughness as to enable a sample, e.g. a urine sample to be injected directly onto the reagent layer formed thereon, not via such a vessel as a cup. The resin coat provided on the back surface of the support is designed to reduce the degree of sagging or warping by wetting of the body fluid assay strip, while the assay result is determined.

The coat-forming composition according to this invention comprises an alcoholic solvent solution of a mixed resin of a water-insoluble but alcohol-soluble resin capable of forming a film showing a saturation hygroscopicity less than 15% at a 90% relative humidity with a water-soluble and alcohol-soluble resin capable of forming a film showing a saturation hygroscopicity of 15% or more at a 90% relative humidity. By processing that composition by coating or casting, it is thus possible to easily obtain a coat which can retain its film form stably in water for a certain short period of time without being swollen on its surface. It is also possible to obtain a resin coat having a water solubility or water swelling properties enough to be allowed to flow in water, e.g. a coat film which can be used with body fluid assay strips, curl fit films for hydraulic transfer, etc. so as to afford the desired water solubility or water swelling properties to them, but enables their form to be stably retained in water for a sufficient, if not long, period of time.

EXAMPLE C

In what follows, the illustrative construction of the resin-coated material according to this invention and how to use it will be explained with reference to an embodiment in which said material is used as the support for a body fluid assay strip.

Preparation of Water-Soluble or -Dispersible Fibrous Material

A mixed feed of 80 parts by weight of fibrous carboxymethylcellulose having a degree of etherification of 0.54 and 20 parts by weight of bleached kraft pulp was processed to a degree of beating of 20° SR into a starting material for paper making. This starting material was formed into sizeless paper at a rate of 20 m/min by means of a cylinder paper machine, while an 8% by weight aqueous solution of soda carbonate was coated on the wet paper being formed, thereby obtaining alkaline paper (A) having a weight of 120 g/m$^2$.

Subsequently, a 1.25% by weight dilute acid solution of acetic acid and citric acid (at a weight ratio of 2:3) dissolved in a mixture of equal amounts of methanol and water was roll-coated on the paper (A) to a coverage of 1.9 g/m$^2$, calculated as acid matter, followed by drying. In this way, neutral paper (B) was obtained.

The thus obtained paper (B) shows pH 5.8 on its acid treated surface, and provides an aqueous dispersion of pH 7.2. The alkaline paper (A) has a volume of base substitution of 2.79 meq/g (as calculated), and the neutral paper (B) shows a degree of base saturation of 65.1%.

Formation of Resin Coat on the Surface of Fibrous Material

Using a mixed resin of 90 parts by weight of polyvinyl pyrrolidone (PVP)—having a mean polymerization degree of about 11,000; Colidone 90 made by BASF AG. and 10 parts by weight of polyvinyl butyral—having a polymerization degree of about 1,700 and a butylation degree of about 65 mol %; Eslec B made by Sekisui Chemical Co., Ltd.), the aforesaid neutral paper (B) was provided on both its sides with resin coats to a coverage of 5.0 g/m$^2$ on dry matter basis, thereby obtaining a resin-coated material embodying this invention.

Reference will now be made to the coating agent and manner used for forming the aforesaid coats.

Coating Agent

To obtain this, a given amount of a well-stirred mixture of 15% by weight polyvinyl pyrrolidone with amyl alcohol and a given amount of a well-stirred mixture of 15% by weight of polyvinyl butyral with amyl alcohol, both mixtures obtained with the use of a homomixer, were fully mixed together by means of a spatula.

Coating Manner

Coating was carried out with the use of a Miya bar No. 6.

The obtained resin-coated material embodying this invention has a water dispersibility enough to be flushed down the toilet, and the resin coat formed on its surface possesses such a surface toughness so as to enable a fluid body sample to be injected from a syringe onto the reagent layer formed thereon, i.e. such a surface toughness as to enable a sample, e.g. a urine sample to be injected directly onto the reagent layer formed thereon, not via such a vessel as a cup. The resin coat provided on the back surface of this material is designed to reduce the degree of sagging or warping by wetting of the body fluid assay strip, while the assay result is determined.

The aforesaid resin-coated material according to this invention comprises a water-soluble and -dispersible fibrous material and a water-soluble and -dispersible resin coat formed on at least one surface thereof, said resin coat comprising an alcoholic solvent solution of a mixed resin of at least one water-insoluble but alcohol-soluble resin capable of forming a film showing a saturation hygroscopicity of 15% or less at a 90% relative humidity with at least one water-soluble and alcohol-soluble resin capable of forming a film showing a saturation hygroscopicity of 15% or more at a 90% relative humidity.

That is, a resin coat, which can retain its film form stably in water for a certain short period of time without being swollen on its surface and has water-solubility and water-swelling properties enough to be allowed to flow in water, is formed by a coating agent comprising an alcoholic solvent solution. In other words, a resin coat, which has the desired water-swelling properties and water-solubility and can retain its film form stably in water for a sufficient, if not long, length of time, can be easily obtained by coating.

EXAMPLE D

The illustrative construction of the fluid body assay strip according to this invention will now be explained with reference to how to prepare it.

Water-Dispersible or -Soluble Fibrous Material

A mixed feed of 80 parts by weight of fibrous carboxymethylcellulose having a degree of etherification of 0.54 and 20 parts by weight of bleached kraft pulp was processed to a degree of beating of 20° SR into a starting material for paper making. This starting material was formed into sizeless paper at a rate of 20 m/min by means of a cylinder paper machine, while an 8% by weight aqueous solution of carbonate of soda was coated on the wet paper being formed, thereby obtaining alkaline paper (A) having a weight of 120 g/m$^2$.

Subsequently, a 1.25% by weight dilute acid solution of acetic acid and citric acid (at a weight ratio of 2:3) dissolved in a mixture of equal amounts of methanol and water was roll-coated on the paper (A) to a coverage of 1.9 g/m$^2$, calculated as acid matter, followed by drying. In this way, neutral paper (B) was obtained.

The thus obtained paper (B) shows pH 5.8 on its acid treated surface, and provides an aqueous dispersion of pH 7.2. The alkaline paper (A) has a volume of base substitution of 2.79 meq/g (as calculated), and the neutral paper (B) shows a degree of base saturation of 65.1%.

Formation of Resin Coat on the Surface of Fibrous Material

Using a mixed resin of 90 parts by weight of polyvinyl pyrrolidone (PVP)—having a mean polymerization degree of about 11,000; Colidone 90 made by BASF AG. and 10 parts by weight of polyvinyl butyral (Bx-1) having a polymerization degree of about 1,700 and a butylation degree of about 65 mol %; Eslec B made by Sekisui Chemical Co., Ltd.) in the amounts indicated in Table 1, the aforesaid neutral paper (B) was provided on one surface with a resin coat to a coverage of 5.0 g/m$^2$ on dry matter basis, thereby obtaining supports for body fluid assay strips.

Reference will now be made to the coating agent and manner used for forming the aforesaid coats.

Coating Agent

To obtain this, a given amount of a well-stirred mixture of 15% by weight polyvinyl pyrrolidone with amyl alcohol and a given amount of a well-stirred mixture of 15% by weight of polyvinyl butyral with amyl alcohol, both mixtures obtained with the use of a homomixer, were fully mixed together by means of a spatula.

Coating Manner

Coating was carried out with the use of a Miya bar No. 1.

TABLE 1

| Type of Supports | Composition of Surface Resin Coats | |
|---|---|---|
| | (PVP) | (Bx-1) |
| (a-1) | 100 | 0 |
| (a-2) | 95 | 5 |
| (a-3) | 90 | 10 |
| (a-4) | 80 | 20 |
| (a-5) | 70 | 30 |
| (a-6) | 60 | 40 |
| (a-7) | 50 | 50 |
| (a-8) | 30 | 70 |

In the instant example, the aforesaid supports (a-1) to (a-8) for body fluid assay strips were used along with a control support formed of the aforesaid paper (B). Each of the resin-coated supports was designed such that when it was cut into a rectangular flat strip of 8 mm ×80 mm, a square flat region of 5 mm ×5 mm to receive a reagent layer was left in the vicinity of the strip's end. A glucose assay reagent layer composed of the following components was printed on that region by means of an 8-mesh screen printing plate.

| Composition for Glucose Assay Reagent | |
|---|---|
| Glucose oxidase | 3.6 p.b.w. |
| Peroxidase | 2.4 p.b.w. |
| Guaiac fat | 4.8 p.b.w. |
| Sorbitan monolaurate | 7.2 p.b.w. |
| L-ascorbyl stearate | 0.24 p.b.w. |
| Citric acid | 2.8 p.b.w. |
| Soda citrate | 11.0 p.b.w. |
| Polyvinyl pyrrolidone (Colidone 90 made by BASF AG) | 12.6 p.b.w. |
| Polyvinyl butyral (Eslec BX-1 made by Sekisui Chemical Co., Ltd.) | 2.25 p.b.w. |
| Fine cellulose powders (Abycell TG-D made by Asahi Chemical Industry, Co., Ltd.) | 171 p.b.w. |
| n-Amyl alcohol | 171 p.b.w. |
| Butyl Cellosolve acetate | 67 p.b.w. |

Each of the aforesaid supports provided with the reagent layers was cut into rectangular flat strips of 8 mm ×80 mm, having square flat reagent layers of 5 mm ×5 mm near their ends, thereby obtaining body fluid assay strips embodying this invention. In similar manners, a control strip was obtained.

Experiment 3

About 500 cc of water placed in a beaker were agitated by means of a stirrer until 3 to 4-cm high, stable vortices were obtained. Then, each of the body fluid assay strips of (8 mm ×80 mm) was put in water to measure the length of time (seconds) required for it to disperse in discrete lumps.

The obtained results of the water-solubility and dispersibility tests of the strips are reported in Table 2.

It is understood that an index to whether or not the strips can be flushed down the toilet is at most 700 seconds in terms of the length of time required for them to disperse in discrete lumps.

TABLE 2

| Type of Supports for Assay Strips | Dispersing time (sec.) |
|---|---|
| (a-1) | 13 |
| (a-2) | 16 |
| (a-3) | 20 |
| (a-4) | 33 |
| (a-5) | 55 |
| (a-6) | 100 |
| (a-7) | 300 |
| (a-8) | undispersed |
| (B) | 13 |

Experiment 4

Each of the body fluid assay strips obtained in the above-mentioned examples and comparative example was fixed at the end opposite to the reagent layer carrying end, and tilted and held at an angle of 45° with respect to horizontal. With a syringe spaced 10 mm away from the strip, 3 ml of water was sprayed onto the central region—located about 40 mm away from the reagent layer carrying end—of the reagent layer carrying side of the strip for 2 seconds, followed by two water injections. Then, the strip was held horizontally for 60 seconds. After that, how much the strip was marred on the surface was observed. It was found that the control support (B) and the support (a-1) treated on the surface with 100% polyvinyl pyrrolidone resin were both marred on the reagent layer carrying surfaces However, the surface coats of other supports were found to have a water resistance sufficient to stand up to the syringe tests.

Experiment 5

Two supports (a-1) and (a-1), . . . , or two supports (B) and (B) were put on each other while their reagent layers were brought in contact with each other. While a load of 20 g/cm$^2$ was applied over the strip laminate from above, it was allowed to stand in an atmosphere of 40° C. and 50% RH for 12 hours. After that, one strip was released from the other by a finger tip to observe whether or not blocking took place. The results are reported in Table 3.

TABLE 3

| Type of Supports for Assay Strips | Blocking |
|---|---|
| (a-1) | Blocking occurred |
| (a-2) | No blocking |

TABLE 3-continued

| Type of Supports for Assay Strips | Blocking |
| --- | --- |
| (a-3) | No blocking |
| (a-4) | No blocking |
| (a-5) | No blocking |
| (a-6) | No blocking |
| (a-7) | No blocking |
| (a-8) | No blocking |
| (B) | No blocking |

Likewise, two supports (a-1) and (a-1), ..., or two supports (B) and (B) were put on each other while the reagent layer side of one strip was brought in contact with the reagent layer-free side of the other. In similar manners as mentioned above, whether or not blocking took place was observed. It was found that all the strips showed no sign of blocking whatsoever.

EXAMPLE E

Water-Dispersible or -Soluble Fibrous Material

A mixed feed of 80 parts by weight of fibrous carboxymethylcellulose having a degree of etherification of 0.54 and 20 parts by weight of bleached kraft pulp was processed to a degree of beating of 20° SR into a starting material for paper making. This starting material was formed into sizeless paper at a rate of 20 m/min by means of a cylinder paper machine, while an 8% by weight aqueous solution of soda carbonate was coated on the wet paper being formed, thereby obtaining alkaline paper (A) having a weight of 120 g/m$^2$.

Subsequently, a 1.25% by weight dilute acid solution of acetic acid and citric acid (at a weight ratio of 2:3) dissolved in a mixture of equal amounts of methanol and water was roll-coated on the paper (A) to a coverage of 1.9 g/m$^2$, calculated as acid matter, followed by drying. In this way, neutral paper (B) was obtained.

The thus obtained paper (B) shows pH 5.8 on its acid treated surface, and provides an aqueous dispersion of pH 7.2. The alkaline paper (A) has a volume of base substitution of 2.79 meq/g (as calculated), and the neutral paper (B) shows a degree of base saturation of 65.1%.

Formation of Resin Coat on the Surface of Fibrous Material

Using a mixed resin of 90 parts by weight of polyvinyl pyrrolidone (PVP)—having a mean polymerization degree of about 11,000; Colidone 90 made by BASF AG. and 10 parts by weight of polyvinyl butyral(Bx-1) having a polymerization degree of about 1,700 and a butylation degree of about 65mol %; Eslec B made by Sekisui Chemical Co., Ltd.) in the amounts indicated in Table 1, the aforesaid neutral paper (B) was provided on one surface with a resin coat to a coverage of 5.0 g/m$^2$ on dry matter basis. After that, that paper was provided on the other side with a coat 5.0 g/m$^2$ on dry basis—formed of resins indicated in Table 4, thereby obtaining supports for body fluid assay strips.

Reference will now be made to the coating agent and manner used for forming the aforesaid coats.

Coating Agent

To obtain this, a given amount of a well-stirred mixture of 15% by weight of polyvinyl pyrrolidone with amyl alcohol and a given amount of a well-stirred mixture of 15% by weight of polyvinyl butyral with amyl alcohol, both mixtures obtained with the use of a homomixer, were fully mixed together by means of a spatula.

Coating Manner

Coating was carried out with the use of a Miya bar No. 6.

TABLE 4-1

Back-Surface Resin Coat
100% Polyvinyl Pyrrolidone

| Type of Supports | Composition of Surface Resin Coats | |
| --- | --- | --- |
|  | (PVP) | (Bx-1) |
| (b-1) | 100 | 0 |
| (b-2) | 95 | 5 |
| (b-3) | 90 | 10 |
| (b-4) | 80 | 20 |
| (b-5) | 70 | 30 |
| (b-6) | 60 | 40 |
| (b-7) | 50 | 50 |
| (b-8) | 30 | 70 |

TABLE 4-2

Back-Surface Resin Coat
95% Polyvinyl Pyrrolidone
5% Polyvinyl Butyral

| Type of Supports | Composition of Surface Resin Coats | |
| --- | --- | --- |
|  | (PVP) | (Bx-1) |
| (c-1) | 100 | 0 |
| (c-2) | 95 | 5 |
| (c-3) | 90 | 10 |
| (c-4) | 80 | 20 |
| (c-5) | 70 | 30 |
| (c-6) | 60 | 40 |
| (c-7) | 50 | 50 |
| (c-8) | 30 | 70 |

TABLE 4-3

Back-Surface Resin Coat
95% Polyvinyl Pyrrolidone
10% Polyvinyl Butyral

| Type of Supports | Composition of Surface Resin Coats | |
| --- | --- | --- |
|  | (PVP) | (Bx-1) |
| (d-1) | 100 | 0 |
| (d-2) | 95 | 5 |
| (d-3) | 90 | 10 |
| (d-4) | 80 | 20 |
| (d-5) | 70 | 30 |
| (d-6) | 60 | 40 |
| (d-7) | 50 | 50 |
| (d-8) | 30 | 70 |

TABLE 4-4

Back-Surface Resin Coat
80% Polyvinyl Pyrrolidone
20% Polyvinyl Butyral

| Type of Supports | Composition of Surface Resin Coats | |
| --- | --- | --- |
|  | (PVP) | (Bx-1) |
| (e-1) | 100 | 0 |
| (e-2) | 95 | 5 |
| (e-3) | 90 | 10 |
| (e-4) | 80 | 20 |
| (e-5) | 70 | 30 |
| (e-6) | 60 | 40 |
| (e-7) | 50 | 50 |
| (e-8) | 30 | 70 |

TABLE 4-5

Back-Surface Resin Coat
70% Polyvinyl Pyrrolidone
30% Polyvinyl Butyral

| Type of Supports | Composition of Surface Resin Coats | |
|---|---|---|
| | (PVP) | (Bx-1) |
| (f-1) | 100 | 0 |
| (f-2) | 95 | 5 |
| (f-3) | 90 | 10 |
| (f-4) | 80 | 20 |
| (f-5) | 70 | 30 |
| (f-6) | 60 | 40 |
| (f-7) | 50 | 50 |
| (f-8) | 30 | 70 |

TABLE 4-6

Back-Surface Resin Coat
60% Polyvinyl Pyrrolidone
40% Polyvinyl Butyral

| Type of Supports | Composition of Surface Resin Coats | |
|---|---|---|
| | (PVP) | (Bx-1) |
| (g-1) | 100 | 0 |
| (g-2) | 95 | 5 |
| (g-3) | 90 | 10 |
| (g-4) | 80 | 20 |
| (g-5) | 70 | 30 |
| (g-6) | 60 | 40 |
| (g-7) | 50 | 50 |
| (g-8) | 30 | 70 |

TABLE 4-7

Back-Surface Resin Coat
50% Polyvinyl Pyrrolidone
50% Polyvinyl Butyral

| Type of Supports | Composition of Surface Resin Coats | |
|---|---|---|
| | (PVP) | (Bx-1) |
| (h-1) | 100 | 0 |
| (h-2) | 95 | 5 |
| (h-3) | 90 | 10 |
| (h-4) | 80 | 20 |
| (h-5) | 70 | 30 |
| (h-6) | 60 | 40 |
| (h-7) | 50 | 50 |
| (h-8) | 30 | 70 |

TABLE 4-8

No Back-Surface Resin Coat

| Type of Supports | Composition of Surface Resin Coats | |
|---|---|---|
| | (PVP) | (Bx-1) |
| (i-1) | 100 | 0 |
| (i-2) | 95 | 5 |
| (i-3) | 90 | 10 |
| (i-4) | 80 | 20 |
| (i-5) | 70 | 30 |
| (i-6) | 60 | 40 |
| (i-7) | 50 | 50 |
| (i-8) | 30 | 70 |

In the instant example, the aforesaid supports (a-1) to (i-8) for body fluid assay strips were used along with a control support formed of the aforesaid paper (B) provided on both its sides with no coating agent. Each of the resin-coated supports was designed such that when it was cut into a rectangular flat strip of 8 mm ×80 mm, a square flat region of 5 mm ×5 mm to receive a reagent layer was left on the surface coat in the vicinity of the strip's end. A glucose assay reagent layer composed of the following components was printed on that region by means of an 8-mesh screen printing plate.

| Composition for Glucose Assay Reagent | |
|---|---|
| Glucose oxidase | 3.6 p.b.w. |
| Peroxidase | 2.4 p.b.w. |
| Guaiac fat | 4.8 p.b.w. |
| Sorbitan monolaurate | 7.2 p.b.w. |
| L-ascorbyl stearate | 0.24 p.b.w. |
| Citric acid | 2.8 p.b.w. |
| Soda citrate | 11.0 p.b.w. |
| Polyvinyl pyrrolidone (Colidone 90 made by BASF AG) | 12.6 p.b.w. |
| Polyvinyl butyral (Eslec BX-1 made by Sekisui Chemical Co., Ltd.) | 2.25 p.b.w. |
| Fine cellulose powders (Abycell TG-D made by Asahi Chemical Industry, Co., Ltd.) | 171 p.b.w. |
| n-Amyl alcohol | 171 p.b.w. |
| Butyl Cellosolve acetate | 67 p.b.w. |

Each of the aforesaid supports provided with the reagent layers was cut into rectangular flat strips of 8 mm ×80 mm, having square flat reagent layers of 5 mm ×5 mm near their ends, thereby obtaining body fluid assay strips embodying this invention. In similar manners, a control strip was obtained

Experiment 6

About 500 cc of water placed in a beaker were agitated by means of a stirrer until 3 to 4-cm high, stable vortices were obtained. Then, each of the body fluid assay strips of (8 mm ×80 mm) was put in water to measure the length of time (seconds) required for it to disperse in discrete lumps.

The obtained results of the water-solubility and dispersibility tests of the strips are reported in Table 5.

It is understood that an index to whether or not the strips can be flushed down the toilet is not greater than 700 seconds in terms of the length of time required for them to disperse in discrete lumps.

TABLE 5-1

| Type of Supports for Assay Strips | Dispersing time (sec.) |
|---|---|
| (b-1) | 16 |
| (b-2) | 21 |
| (b-3) | 28 |
| (b-4) | 42 |
| (b-5) | 61 |
| (b-6) | 110 |
| (b-7) | 300 |
| (b-8) | undispersed |
| (B) | 13 |

TABLE 5-2

| Type of Supports for Assay Strips | Dispersing time (sec.) |
|---|---|
| (c-1) | 21 |
| (c-2) | 25 |
| (c-3) | 32 |
| (c-4) | 45 |
| (c-5) | 62 |
| (c-6) | 119 |
| (c-7) | 312 |
| (c-8) | undispersed |

TABLE 5-3

| Type of Supports for Assay Strips | Dispersing time (sec.) |
|---|---|
| (d-1) | 28 |
| (d-2) | 32 |
| (d-3) | 37 |
| (d-4) | 49 |
| (d-5) | 67 |
| (d-6) | 130 |

TABLE 5-3-continued

| Type of Supports for Assay Strips | Dispersing time (sec.) |
|---|---|
| (d-7) | 320 |
| (d-8) | undispersed |

TABLE 5-4

| Type of Supports for Assay Strips | Dispersing time (sec.) |
|---|---|
| (e-1) | 43 |
| (e-2) | 46 |
| (e-3) | 49 |
| (e-4) | 57 |
| (e-5) | 70 |
| (e-6) | 150 |
| (e-7) | 345 |
| (e-8) | undispersed |

TABLE 5-5

| Type of Supports for Assay Strips | Dispersing time (sec.) |
|---|---|
| (f-1) | 59 |
| (f-2) | 62 |
| (f-3) | 65 |
| (f-4) | 69 |
| (f-5) | 79 |
| (f-6) | 190 |
| (f-7) | 360 |
| (f-8) | undispersed |

TABLE 5-6

| Type of Supports for Assay Strips | Dispersing time (sec.) |
|---|---|
| (g-1) | 110 |
| (g-2) | 120 |
| (g-3) | 130 |
| (g-4) | 150 |
| (g-5) | 195 |
| (g-6) | 265 |
| (g-7) | 430 |
| (g-8) | undispersed |

TABLE 5-7

| Type of Supports for Assay Strips | Dispersing time (sec.) |
|---|---|
| (h-1) | 300 |
| (h-2) | 310 |
| (h-3) | 320 |
| (h-4) | 340 |
| (h-5) | 370 |
| (h-6) | 440 |
| (h-7) | 600 |
| (h-8) | undispersed |

TABLE 5-8

| Type of Supports for Assay Strips | Dispersing time (sec.) |
|---|---|
| (i-1) | 13 |
| (i-2) | 16 |
| (i-3) | 20 |
| (i-4) | 33 |
| (i-5) | 55 |
| (i-6) | 100 |
| (i-7) | 300 |
| (i-8) | undispersed |

Experiment 7

Each of the body fluid assay strips obtained in the above-mentioned examples and comparative example was fixed at the end opposite to the reagent layer carrying end, and tilted and held at an angle of 45° with respect to horizontal. With a syringe spaced 10 mm away from the strip, 3 ml of water was sprayed onto the central region—located about 40 mm away from the reagent layer carrying end—of the reagent layer carrying side of the strip for 2 seconds, followed by two water injections. Then, the strip was held horizontally for 60 seconds. After that, how much the strip was marred on the surface was observed. It was found that the control support untreated on both its sides and the support treated on the surface with 100% polyvinyl pyrrolidone resin were both marred on the reagent layer carrying surfaces. However, the surface coats of other supports were found to have a water resistance sufficient to stand up to the syringe tests.

Experiment 8

In similar manners as explained in Experiment 7, each of the body fluid assay strips obtained in the above-mentioned examples and comparative example was fixed at the end opposite to the reagent layer carrying end, and tilted and held at an angle of 45° with respect to horizontal. With a syringe spaced 10 mm away from the strip, 3 ml of water was sprayed onto the central region—located about 40 mm away from the reagent layer carrying end—of the reagent layer carrying side of the strip for 2 seconds, followed by two water injections. Then, the strip was hold horizontally for 60 seconds, after which the angle -$\theta$- of sagging of the strip was measured.

The results are reported in Table 6, in which the angle $\theta$ of sagging of the strip refers to the angle of bending of the reagent layer-free side of the strip.

At an angle $\theta$ smaller than 110 or at a larger angle of sagging, the assay strip offers a handling problem when a body fluid sample is injected directly onto the strip, because considerable difficulty is involved in confirming its color changes.

TABLE 6-1

| Type of Supports | Angle $\theta$ |
|---|---|
| (b-1) | 102 |
| (b-2) | 110 |
| (b-3) | 118 |
| (b-4) | 124 |
| (b-5) | 130 |
| (b-6) | 132 |
| (b-7) | 138 |

TABLE 6-2

| Type of Supports | Angle $\theta$ |
|---|---|
| (c-1) | 111 |
| (c-2) | 116 |
| (c-3) | 118 |
| (c-4) | 125 |
| (c-5) | 130 |
| (c-6) | 132 |
| (c-7) | 137 |

TABLE 6-3

| Type of Supports | Angle $\theta$ |
|---|---|
| (d-1) | 118 |
| (d-2) | 119 |
| (d-3) | 120 |
| (d-4) | 129 |
| (d-5) | 134 |
| (d-6) | 134 |
| (d-7) | 137 |

TABLE 6-4

| Type of Supports | Angle θ |
|---|---|
| (e-1) | 124 |
| (e-2) | 126 |
| (e-3) | 132 |
| (e-4) | 142 |
| (e-5) | 145 |
| (e-6) | 146 |
| (e-7) | 146 |

TABLE 6-5

| Type of Supports | Angle θ |
|---|---|
| (f-1) | 130 |
| (f-2) | 133 |
| (f-3) | 140 |
| (f-4) | 149 |
| (f-5) | 155 |
| (f-6) | 155 |
| (f-7) | 156 |

TABLE 6-6

| Type of Supports | Angle θ |
|---|---|
| (g-1) | 134 |
| (g-2) | 138 |
| (g-3) | 142 |
| (g-4) | 150 |
| (g-5) | 153 |
| (g-6) | 159 |
| (g-7) | 159 |

TABLE 6-7

| Type of Supports | Angle θ |
|---|---|
| (h-1) | 140 |
| (h-2) | 144 |
| (h-3) | 149 |
| (h-4) | 150 |
| (h-5) | 155 |
| (h-6) | 158 |
| (h-7) | 160 |

TABLE 6-8

| Type of Supports | Angle θ |
|---|---|
| (i-1) | 90 |
| (i-2) | 90 |
| (i-3) | 90 |
| (i-4) | 90 |
| (i-5) | 90 |
| (i-6) | 90 |
| (i-7) | 90 |

EXAMPLE F

Coating Agent

To obtain this, a given amount of a well-stirred mixture of 15% by weight of polyvinyl pyrrolidone with 1,4-dioxane and a given amount of a well-stirred mixture of 15% by weight of polyvinyl butyral with 1,4-dioxane, both mixtures obtained with the use of a homomixer, were fully mixed together by means of a spatula.

Coating Manner

Coating was carried out with the use of a Miya bar No. 6.

In the instant example, the aforesaid supports (j-1) to (j-8) for body fluid assay strips, set out in Table 7, were used along with a control support formed of the aforesaid paper (B). Each of the resin-coated supports was designed such that when it was cut into a rectangular flat strip of 8 mm × 80 mm, a square flat region of 5 mm × 5 mm to receive a reagent layer was left in the vicinity of the strip's end. A glucose assay reagent layer composed of the following components was printed on that region by means of an 8-mesh screen printing plate.

| Composition for Glucose Assay Reagent | |
|---|---|
| Glucose oxidase | 3.6 p.b.w. |
| Peroxidase | 2.4 p.b.w. |
| Guaiac fat | 4.8 p.b.w. |
| Sorbitan monolaurate | 7.2 p.b.w. |
| L-ascorbyl stearate | 0.24 p.b.w. |
| Citric acid | 2.8 p.b.w. |
| Soda citrate | 11.0 p.b.w. |
| Polyvinyl pyrrolidone (Colidone 90 made by BASF AG) | 12.6 p.b.w. |
| Polyvinyl butyral (Eslec BX-1 made by Sekisui Chemical Co., Ltd.) | 2.25 p.b.w. |
| Fine cellulose powders (Abycell TG-D made by Asahi Chemical Industry, Co., Ltd.) | 171 p.b.w. |
| n-Amyl alcohol | 171 p.b.w. |
| Butyl Cellosolve acetate | 67 p.b.w. |

Each of the aforesaid supports provided with the reagent layers was cut into rectangular flat strips of 8 mm × 80 mm, having square flat reagent layers of 5 mm × 5 mm near their ends, thereby obtaining body fluid assay strips embodying this invention. In similar manners, a control strip was obtained.

Experiment 9

About 500 cc of water placed in a beaker were agitated by means of a stirrer until 3 to 4-cm high, stable vortices were obtained. Then, each of the body fluid assay strips of (8 mm × 80 mm) was put in water to measure the length of time (seconds) required for it to disperse in discrete lumps.

The obtained results of the strips' water-solubility and -dispersibility tests are reported in Table 8.

It is understood that an index to whether or not the strips can be flushed down the toilet is at most 700 seconds in terms of the length of time required for them to disperse in discrete lumps.

TABLE 7

| | Composition of Surface Resin Coats | |
|---|---|---|
| Type of Supports | (PVP) | (Bx-1) |
| (j-1) | 100 | 0 |
| (j-2) | 95 | 5 |
| (j-3) | 90 | 10 |
| (j-4) | 80 | 20 |
| (j-5) | 70 | 30 |
| (j-6) | 60 | 40 |
| (j-7) | 50 | 50 |
| (j-8) | 30 | 70 |

TABLE 8

| Type of Supports for Assay Strips | Dispersing time (sec.) |
|---|---|
| (j-1) | 13 |
| (j-2) | 16 |
| (j-3) | 21 |
| (j-4) | 35 |
| (j-5) | 57 |
| (j-6) | 100 |
| (j-7) | 300 |
| (j-8) | undispersed |
| (B) | 13 |

Experiment 10

Each of the body fluid assay strips obtained in the above-mentioned examples and comparative example was fixed at the end opposite to the reagent layer carrying end, and tilted and held at an angle of 45° with respect to horizontal. With a syringe spaced 10 mm away from the strip, 3 ml of water was sprayed onto the central region—located about 40 mm away from the reagent layer carrying end—of the reagent layer carrying side of the strip for 2 seconds, followed by two water injections. Then, the strip was hold horizontally for 60 seconds. After that, how much the strip was marred on the surface was observed. It was found that the untreated control support (B) and the support (j-1) treated on the surface with 100% polyvinyl pyrrolidone resin were both marred on the reagent layer carrying surfaces. However, the surface coats of other supports were found to have a water resistance sufficient to stand up to the syringe tests. Experiment 11

Two supports (j-1) and (j-1), . . . , or two supports (B) and (B) were put on each other while their reagent layers were brought in contact with each other. While a load of 20 g/cm² was applied over the strip laminate from above, it was allowed to stand in an atmosphere of 40° C. and 50% RH for 12 hours. After that, one strip was released from the other by a finger tip to observe whether or not blocking took place.

The results are reported in Table 9.

TABLE 9

| Type of Supports for Assay Strips | Blocking |
| --- | --- |
| (j-1) | Blocking occurred |
| (j-2) | No blocking |
| (j-3) | No blocking |
| (j-4) | No blocking |
| (j-5) | No blocking |
| (j-6) | No blocking |
| (j-7) | No blocking |
| (j-8) | No blocking |
| (B) | No blocking |

Likewise, two supports (j-1) and (j-1), . . . , or two supports (B) and (B) were put on each other while the reagent layer side of one strip was brought in contact with the reagent layer-free side of the other. In similar manners as mentioned above, whether or not blocking took place was observed. It was found that all the strips showed no sign of blocking whatsoever.

EXAMPLE G

Formation of Resin Coat on the Surface of Fibrous Material

The above-mentioned neutral paper (B) was coated on one surface with each of the mixed resins indicated in Table 10 (to a thickness of about 30 μm and a coverage of 5.0 g/m² on dry matter basis). After that, its back surface was coated with each of the same mixed resins (to a thickness of about 30 μm and a coverage of 25.0 g/m² on dry matter basis) to obtain a body fluid assay strip support.

Coating Agent

To obtain this, a given amount of a well-stirred mixture of 15% by weight of polyvinyl pyrrolidone with 1,4-dioxane and a given amount of a well-stirred mixture of 15% by weight of polyvinyl butyral with 1,4-dioxane, both mixtures obtained with the use of a homomixer, were fully mixed together by means of a spatula Coating Manner A 5.0-g/m² coating-drying cycle was repeated five times with a Miya bar No. 6 to obtain a coat about five times greater in thickness than those of Examples A–F.

In the instant example, the supports (k-1) to (k-8) for body fluid assay strips, indicated in Table 10, were used along with a control support formed of the aforesaid paper (B) provided on both its sides with no coating agent. Each of the resin-coated supports was designed such that when it was cut into a rectangular flat strip of 8 mm ×80 mm, a square flat region of 5 mm ×5 mm to receive a reagent layer was left on the surface coat in the vicinity of the strips end. A glucose assay reagent layer composed of the following components was printed on that region by means of an 8-mesh screen printing plate.

| Composition for Glucose Assay Reagent | |
| --- | --- |
| Glucose oxidase | 3.6 p.b.w. |
| Peroxidase | 2.4 p.b.w. |
| Guaiac fat | 4.8 p.b.w. |
| Sorbitan monolaurate | 7.2 p.b.w. |
| L-ascorbyl stearate | 0.24 p.b.w. |
| Citric acid | 2.8 p.b.w. |
| Soda citrate | 11.0 p.b.w. |
| Polyvinyl pyrrolidone (Colidone 90 made by BASF AG) | 12.6 p.b.w. |
| Polyvinyl butyral (Eslec BX-1 made by Sekisui Chemical Co., Ltd.) | 2.25 p.b.w. |
| Fine cellulose powders (Abycell TG-D made by Asahi Chemical Industry, Co., Ltd.) | 171 p.b.w. |
| n-Amyl alcohol | 171 p.b.w. |
| Butyl Cellosolve acetate | 67 p.b.w. |

Each of the aforesaid supports provided with the reagent layers was cut into rectangular flat strips of 8 mm ×80 mm, having square flat reagent layers of 5 mm ×5 mm near their ends, thereby obtaining body fluid assay strips embodying this invention. In similar manners, a control strip was obtained.

Experiment 12

About 500 cc of water placed in a beaker were agitated by means of a stirrer until 3 to 4-cm high, stable vortices were obtained. Then, each of the body fluid assay strips of (8 mm ×80 mm) was put in water to measure the length of time (seconds) required for it to disperse in discrete lumps.

The obtained results of the water-solubility and dispersibility tests of the strips are reported in Table 11.

It is understood that an index to whether or not the strips can be flushed down the toilet is not greater than 700 seconds in terms of the length of time required for them to disperse in discrete lumps.

TABLE 10

| | Composition of Surface Resin Coats | |
| --- | --- | --- |
| Type of Supports | (PO) | (Bx-1) |
| (k-1) | 100 | 0 |
| (k-2) | 95 | 5 |
| (k-3) | 90 | 10 |
| (k-4) | 80 | 20 |
| (k-5) | 70 | 30 |
| (k-6) | 60 | 40 |
| (k-7) | 50 | 50 |
| (k-8) | 30 | 70 |

TABLE 11

| Type of Supports for Assay Strips | Dispersing time (sec.) |
| --- | --- |
| (k-1) | 16 |
| (k-2) | 25 |
| (k-3) | 38 |
| (k-4) | 60 |
| (k-5) | 80 |
| (k-6) | 280 |
| (k-7) | 700 |
| (k-8) | undispersed |
| (B) | 13 |

Experiment 13

Each of the body fluid assay strips obtained in the above-mentioned examples and comparative example was fixed at the end opposite to the reagent layer carrying end, and tilted and held at an angle of 45° with respect to horizontal. With a syringe spaced 10 mm away from the strip, 3 ml of water was sprayed onto the central region—located about 40 mm away from the reagent layer carrying end—of the reagent layer carrying side of the strip for 2 seconds, followed by two water injections. Then, the strip was hold horizontally for 60 seconds. After that, how much the strip was marred on the surface was observed. It was found that the control support untreated on both its sides and the support (k-1) treated on the surface with 100% polyvinyl pyrrolidone resin were both marred on the reagent layer carrying surfaces. However, the surface coats of other supports were found to have a water resistance sufficient to stand up to the syringe tests.

Experiment 14

Two supports (k-1) and (k-1) . . . , or two supports (B) and (B) were put on each other while their reagent layers were brought in contact with each other. While a load of 20 g/cm$^2$ was applied over the strip laminate from above, it was allowed to stand in an atmosphere of 40° C. and 50% RH for 12 hours. After that, one strip was released from the other by a finger tip to observe whether or not blocking took place.

The results are reported in Table 12.

TABLE 12

| Type of Supports for Assay Strips | Blocking |
| --- | --- |
| (k-1) | Blocking occurred |
| (k-2) | No blocking |
| (k-3) | No blocking |
| (k-4) | No blocking |
| (k-5) | No blocking |
| (k-6) | No blocking |
| (k-7) | No blocking |
| (k-8) | No blocking |
| (B) | No blocking |

Likewise, two supports (k-1) and (k-1), . . . , or two supports (B) and (B) were put on each other while the reagent layer side of one strip was brought in contact with the reagent layer-free side of the other. In similar manners as mentioned above, whether or not blocking took place was observed. It was found that all the strips showed no sign of blocking whatsoever.

EXAMPLE H

Using each of the mixed resins of polyethylene oxide (PO) (POLYOX WSR N-750 made by Union Carbide Co, Ltd.) with polyvinyl butyral (Bx-1) (Eslec Bx-1 made of Sekisui Chemical Co., Ltd.), the neutral paper (B) obtained from the water-dispersible and -soluble fibrous material of Example F was coated to a coverage of 5.0 g/m$^2$ on dry matter basis to obtain a body fluid assay strip support.

Coating Agent

To obtain this, a given amount of a well-stirred mixture of 15% by weight of polyvinyl pyrrolidone with 1,4-dioxane and a given amount of a well-stirred mixture of 15% by weight of polyvinyl butyral with 1,4-dioxane, both mixtures obtained with the use of a homomixer, were fully mixed together by means of a spatula.

Coating Manner

Coating was effected with a Miya bar No. 6.

TABLE 13

| Type of Supports | Composition of Surface Resin Coats | |
| --- | --- | --- |
| | (PO) | (Bx-1) |
| (l-1) | 100 | 0 |
| (l-2) | 95 | 5 |
| (l-3) | 90 | 10 |
| (l-4) | 80 | 20 |
| (l-5) | 70 | 30 |
| (l-6) | 60 | 40 |
| (l-7) | 50 | 50 |
| (l-8) | 30 | 70 |

Using the above-mentioned supports (l-1) to (l-8) and the control support made of the above-mentioned paper (B), body fluid assay strips were obtained together with a control one in similar manners as mentioned in Example F.

Experiment 15

The results of experimentation carried out by following the procedures of Example F are reported in Table 14.

TABLE 14

| Type of Supports for Assay Strips | Dispersing time (sec.) |
| --- | --- |
| (l-1) | 15 |
| (l-2) | 20 |
| (l-3) | 30 |
| (l-4) | 45 |
| (l-5) | 75 |
| (l-6) | 150 |
| (l-7) | 400 |
| (l-8) | undispersed |
| (B) | 13 |

Experiment 16

Experimentation was performed by following the procedures of Example F. It was found that the control support (B) untreated on both its sides and the support (l-1) treated on the surface with 100% polyvinyl pyrrolidone resin were both marred on the reagent layer carrying surfaces. However, the surface coats of other supports were found to have a water resistance sufficient to stand up to the syringe tests. Experiment 17

Two supports (l-1) and (l-1), . . . , or two supports (B) and (B) were put on each other while their reagent layers were brought in contact with each other. While a load of 20 g/cm$^2$ was applied over the strip laminate from above, it was allowed to stand in an atmosphere of 40° C. and 50% RH for 12 hours. After that, one strip was released from the other by a finger tip to observe whether or not blocking took place.

The results are reported in Table 15.

TABLE 15

| Type of Supports for Assay Strips | Blocking |
| --- | --- |
| (l-1) | No blocking |
| (l-2) | No blocking |
| (l-3) | No blocking |
| (l-4) | No blocking |
| (l-5) | No blocking |
| (l-6) | No blocking |
| (l-7) | No blocking |
| (l-8) | No blocking |
| (B) | No blocking |

Likewise, two supports (l-1) and (l-1), . . . , or two supports (B) and (B) were put on each other while the reagent layer side of one strip was brought in contact with the reagent layer-free side of the other. In similar manners as mentioned above, whether or not blocking took place was observed. It was found that all the strips showed no sign of blocking whatsoever.

EXAMPLE I

Formation of Resin Coat on the Surface of Fibrous Material

Using each of the mixed resins of polyethylene oxide (PO) (POLYOX WSR N-750 made by Union Carbide Co, Ltd.) with polyvinyl butyral (Bx-1) (Eslec Bx-1 made of Sekisui Chemical Co., Ltd.), the neutral paper (B) obtained from the water-dispersible and -soluble fibrous material of Example E was coated one surface to a thickness of about 30 μm and a coverage of 25.0 g/m$^2$ on dry matter basis. After that, the paper was coated on the back surface with the same mixed resin to the same thickness and coverage to obtain a body fluid assay strip support.

It is noted that the coating agent and manner used for forming the above-mentioned resin coats are:

Coating Agent

To obtain this, a given amount of a well-stirred mixture of 15% by weight of polyethylene oxide with 1,4-dioxane and a given amount of a well-stirred mixture of 15% by weight of polyvinyl butyral with 1,4-dioxane, both mixtures obtained with the use of a homomixer, were fully mixed together by means of a spatula.

Coating Manner

A 5.0-g/m$^2$ coating-drying cycle was repeated five times with a Miya bar No. 6 to obtain a coat about five times greater in thickness than those of Examples A–F.

TABLE 16

| Type of Supports | Composition of Surface Resin Coats | |
| --- | --- | --- |
| | (PO) | (Bx-1) |
| (m-1) | 100 | 0 |
| (m-2) | 95 | 5 |
| (m-3) | 90 | 10 |
| (m-4) | 80 | 20 |
| (m-5) | 70 | 30 |
| (m-6) | 60 | 40 |
| (m-7) | 50 | 50 |
| (m-8) | 30 | 70 |

Using the above-mentioned supports (m-1) to (m-8) and the control support made of the above-mentioned paper (B), body fluid assay strips were obtained together with a control one in similar manners as mentioned in Example F.

Experiment 18

The results of experimentation carried out by following the procedures of Example F are reported in Table 14.

TABLE 17

| Type of Supports for Assay Strips | Dispersing time (sec.) |
| --- | --- |
| (m-1) | 16 |
| (m-2) | 30 |
| (m-3) | 45 |
| (m-4) | 75 |
| (m-5) | 110 |
| (m-6) | 300 |
| (m-7) | 700 |
| (m-8) | undispersed |
| (B) | 13 |

Experiment 19

Experimentation was performed by following the procedures of Example F. It was found that the control support (B) untreated on both its sides and the support (m-1) treated on the surface with 100% polyvinyl pyrrolidone resin were both marred on the reagent layer carrying surfaces. However, the surface coats of other supports were found to have a water resistance sufficient to stand up to the syringe tests.

Experiment 20

Two supports (m-1) and (m-1), . . . , or two supports (B) and (B) were put on each other while their reagent layers were brought in contact with each other. While a load of 20 g/cm$^2$ was applied over the strip laminate from above, it was allowed to stand in an atmosphere of 40° C. and 50% RH for 12 hours. After that, one strip was released from the other by a finger tip to observe whether or not blocking took place.

The results are reported in Table 18.

TABLE 18

| Type of Supports for Assay Strips | Blocking |
| --- | --- |
| (m-1) | No blocking |
| (m-2) | No blocking |
| (m-3) | No blocking |
| (m-4) | No blocking |
| (m-5) | No blocking |
| (m-6) | No blocking |
| (m-7) | No blocking |
| (m-8) | No blocking |
| (B) | No blocking |

Likewise, two supports (m-1) and (m-1), . . . , or two supports (B) and (B) were put on each other while the reagent layer side of one strip was brought in contact with the reagent layer-free side of the other. In similar manners as mentioned above, whether or not blocking took place was observed. It was found that all the strips showed no sign of blocking whatsoever.

The body fluid assay unit according to this invention comprises a support including a water-soluble and -dispersible fibrous substrate and a water-soluble and dispersible resin coat formed on one surface of said substrate and a body fluid assay reagent layer formed on the surface of said resin coat provided on said fibrous substrate. That water-soluble and -dispersible resin coat formed on the one surface of said water-soluble and dispersible fibrous substrate comprises a mixed resin of 50 to 95 parts by weight of a water-soluble resin with 50 to 5 parts by weight of a polymeric water-insoluble resin, and that reagent layer is formed of a coat layer using a resin as a vehicle.

In the present body fluid assay device of such construction as mentioned above, the support is formed by the paper-making step and the step of applying a coating agent to the paper. Thus, the support is easy to manufacture. In addition, while the support possesses the rigidity required to serve as a body fluid assay unit support, it is so well soluble and dispersible in water that, after use, it can be sanitarily and easily disposed of in toilet facilities.

In the body fluid assay device according to this invention, the assay reagent layer formed of a coat layer is provided on the surface of the resin coat on the support's surface. When forming the assay reagent layer, it is thus unlikely that the coating agent for forming the assay reagent layer may penetrate through the support. Accordingly, this assay reagent layer is well colored.

In the body fluid assay device according to this invention, the assay reagent layer is formed of a coat layer in which the same type of resin as the resin component of the coat layer formed on the supports surface is used as a vehicle. Thus, increased adhesion is obtained between the support and the assay reagent layer.

It is noted that since the assay reagent layer on the body fluid assay device according to this invention is formed of a coat layer in which a mixed resin of a water-soluble resin with a water-insoluble resin is used as a vehicle, a solvent having a suitable degree of dryness can be used for obtaining an assay reagent layer-forming ink composition used when forming the assay reagent layer on the support. This ink composition has good printability, etc.

Since the support is coated with a specific resin coat, the body fluid assay unit according to this invention possesses such toughness as to enable a body fluid sample to be injected from a syringe onto the reagent layer, i.e. such toughness as to enable a sample, e.g. a urine sample to be inspected by injecting it directly onto the reagent layer, not via a vessel such as a cup. In addition, blocking is prevented from occurring by mixing a highly hygroscopic resin likely to be blocked, such as PVP with a water-insoluble resin.

INDUSTRIAL APPLICABILITY

The water-disintegrable material according to this invention, for instance, may be applicable to formats for confidential papers, frames for raising rice seedlings, seeding sheets, seedling sheets, water-soluble water absorption paper and substrates for body fluid assay devices. Before or during use, it plays a recording medium, delivery, protection or other role while its shape is retained. After use, it can be eventually disposed of by dissolving and dispersing it in water.

We claim:

1. A device for assaying a body fluid comprising:
a support comprising a water-soluble or water-dispersible fibrous substrate;
a water-soluble or water-dispersible resin coat formed on at least one surface of said substrate; and
a body fluid assay reagent layer formed on said water-soluble or water-dispersible resin coat,
said water-soluble or water-dispersible resin coat comprising a mixture of 50 to 95 parts by weight of polyvinyl pyrrolidone and 50 to 5 parts by weight of polyvinyl butyral,
said body fluid assay reagent layer comprising a coat layer using a resin as a vehicle, and
said device having sufficient rigidity to permit assaying to be readily carried out and yet capable, after assaying is carried out, of being water-dispersible or water-soluble to permit the device to be readily broken up or dissolved to be flushed down a toilet.

2. The device of claim 1, wherein said body fluid assay reagent layer is formed of a coat layer using as a vehicle a mixed resin or polyvinyl pyrrolidone with polyvinyl butyral.

3. The device of claim 1, wherein said water-soluble or water-dispersible fibrous substrate comprises a paper comprising fibrous carboxymethylcellulose or carboxyethylcellulose having a degree of etherification of 0.1 to 1.0.

4. The device of claim 3, wherein said fibrous carboxymethylcellulose or carboxyethylcellulose has a degree of base saturation of at least 20% and said paper provides a solution or dispersion having a pH from 5.0 to 8.0

5. A device for assaying a body fluid comprising:
a support comprising a water-soluble or water-dispersible fibrous substrate having a front surface and a back surface;
a water-soluble or water-dispersible resin coat formed on a front surface and a back surface of said substrate; and
a body fluid assay reagent layer formed on said water-soluble or water-dispersible resin coat formed on the front surface of said substrate,
said water-soluble or water-dispersible resin coat formed on the front surface of said substrate comprising a mixture of 50 to 95 parts by weight of polyvinyl pyrrolidone and 50 to 5 parts by weight of polyvinyl butyral,
said water-soluble or water-dispersible resin coat formed on the back surface of said substrate comprising polyvinyl pyrrolidone or a mixed resin of 100 parts by weight of less polyvinyl pyrrolidone with 100 parts by weight or less of polyvinyl butyral,
said body fluid assay reagent layer comprising a coat layer using a resin as a vehicle, and
said device having sufficient rigidity to permit assaying to be readily carried out and yet capable, after assaying is carried out, of being water-dispersible or water-soluble to permit the device to be readily broken up or dissolved to be flushed down a toilet.

6. The device of claim 5, wherein said body fluid assay reagent layer is formed of a coat layer using as a vehicle a mixed resin of polyvinyl pyrrolidone with polyvinyl butyral.

7. The device of claim 5, wherein said water-soluble or water-dispersible fibrous substrate comprises a paper comprising fibrous carboxymethylcellulose or carboxyethylcellulose having a degree of etherification of 0.1 to 1.0.

8. The device of claim 7, wherein said fibrous carboxymethylcellulose or carboxyethylcellulose has a degree of base saturation of at least 20% and said paper provides a solution or dispersion having a pH from 5.0 to 8.0.

* * * * *